United States Patent
Ramello et al.

(10) Patent No.: US 10,196,326 B2
(45) Date of Patent: Feb. 5, 2019

(54) PROCESS FOR THE PRODUCTION OF DIENES

(71) Applicant: versalis S.p.A., San Donato Milanese (MI) (IT)

(72) Inventors: Stefano Ramello, Novara (IT); Vittorio Milanesi, Porto Mantovano (IT); Roberto Buzzoni, Chivasso (IT)

(73) Assignee: versalis S.p.A., San Donato Milanese (MI) (IT)

( * ) Notice: Subject to any disclaimer, the term of this patent is extended or adjusted under 35 U.S.C. 154(b) by 0 days.

(21) Appl. No.: 15/544,720

(22) PCT Filed: Feb. 22, 2016

(86) PCT No.: PCT/IB2016/050932
§ 371 (c)(1),
(2) Date: Jul. 19, 2017

(87) PCT Pub. No.: WO2016/135609
PCT Pub. Date: Sep. 1, 2016

(65) Prior Publication Data
US 2018/0002250 A1    Jan. 4, 2018

(30) Foreign Application Priority Data

Feb. 23, 2015 (IT) .............................. MI2015A0262

(51) Int. Cl.
| | |
|---|---|
| *C07C 1/24* | (2006.01) |
| *B01J 21/12* | (2006.01) |
| *B01J 35/10* | (2006.01) |
| *B01J 37/00* | (2006.01) |
| *C07C 29/60* | (2006.01) |
| *B01J 37/03* | (2006.01) |
| *B01J 37/08* | (2006.01) |
| *B01J 21/08* | (2006.01) |
| *B01J 37/30* | (2006.01) |

(52) U.S. Cl.
CPC ................ *C07C 1/24* (2013.01); *B01J 21/08* (2013.01); *B01J 21/12* (2013.01); *B01J 35/1019* (2013.01); *B01J 37/0018* (2013.01); *B01J 37/033* (2013.01); *B01J 37/08* (2013.01); *B01J 37/30* (2013.01); *C07C 29/60* (2013.01); *C07C 2521/12* (2013.01)

(58) Field of Classification Search
CPC .................................. C07C 29/60; C07C 1/24
See application file for complete search history.

(56) References Cited

U.S. PATENT DOCUMENTS 3,280,209 A * 10/1966 Tonkyn ..................... C07C 1/24
                                                                585/606
2015/0017696 A1   1/2015 Davis et al.
2015/0361007 A1 * 12/2015 Millet .................. C07C 319/20
                                                                526/113

FOREIGN PATENT DOCUMENTS

WO    WO 2013/130481 A1    9/2013

OTHER PUBLICATIONS

Jing et al. Direct Dehydration of 1,3-butanediol into butadiene over aluminosilicate catalysts. Catalysis Science and Technology, 2016, 6, 5830-5840. First Published Feb. 5, 2016. (Year: 2016).*
Haber et al. Manual of Methods and Procedures for Catalyst Characterization. Pure and Applied Chemistry, 1995, 67, 8/9, 1257-1306. (Year: 1995).*
Ray, D.T. Guayule: A source of natural rubber. New crops, pp. 338-343, 1993, Wiley, New York. (Year: 1993).*
Ichikawa et al. Catalytic reaction of 1,3-butanediol over solid acids. Jun. 5, 2006. Elsevier Journal of Molecular Catalysis A: Chemical 256, 106-112 (Year: 2006).*
Nikki Chem. Nikki Catalyst Data Sheet 630-1, N631 L. recorded Apr. 22, 2003. retrieved Mar. 13, 2018. Wayback Machine. https://web.archive.org/web/20030422141033/http://www.nikki-chem.co.jp:80/jpn/products/syokubai/j630-1.html (Year: 2003).*
International Search Report and Written Opinion dated Apr. 25, 2016 in PCT/IB2016/050932.
Ichikawa et al., "Catalytic reaction of 1,3-butanediol over solid acids", Journal of Molecular Catalysts A: Chemical, vol. 256, No. 1-2, XP028015648, 2006, pp. 107-112 (with cover page).
Duan et al., "Efficient production of 1,3-butadiene in the catalytic dehydration of 2,3-butanediol", Applied Catalysis A: General, vol. 491, XP055221056, 2015, pp. 163-169, pp. 164-169 (with cover page).

* cited by examiner

*Primary Examiner* — Philip Y Louie
*Assistant Examiner* — Alyssa L Cepluch
(74) *Attorney, Agent, or Firm* — Oblon, McClelland, Maier & Neustadt, L.L.P.

(57) ABSTRACT

Process for the production of a diene, preferably a conjugated diene, more preferably 1,3-butadiene, comprising the dehydration of at least one alkenol in the presence of at least one catalytic material comprising at least one acid catalyst based on silica ($SiO_2$) and alumina ($Al_2O_3$), preferably a silica-alumina ($SiO_2$-$Al_2O_3$), said catalyst having a content of alumina ($Al_2O_3$) lower than or equal to 12% by weight, preferably ranging from 0.1% by weight to 10% by weight, with respect to the total weight of the catalyst. Preferably, said alkenol can be obtained directly from biosynthesis processes, or through the catalytic dehydration of at least one diol, preferably a butanediol, more preferably 1,3-butanediol, even more preferably bio-1,3-butanediol, deriving from biosynthesis processes. Preferably, said 1,3-butadiene is bio-1,3-butadiene.

14 Claims, No Drawings

PROCESS FOR THE PRODUCTION OF DIENES

The present invention relates to a process for the production of dienes.

More specifically, the present invention relates to a process for the production of a diene, preferably a conjugated diene, more preferably 1,3-butadiene, comprising the dehydration of at least one alkenol in the presence of at least one catalytic material comprising at least one acid catalyst based on silica ($SiO_2$) and alumina ($Al_2O_3$), preferably a silica-alumina ($SiO_2$—$Al_2O_3$), said catalyst having a content of alumina ($Al_2O_3$) lower than or equal to 12% by weight, preferably ranging from 0.1% by weight to 10% by weight, with respect to the total weight of the catalyst.

Preferably, said alkenol can be obtained directly from biosynthesis processes, or through the catalytic dehydration of at least one diol, preferably a butanediol, more preferably 1,3-butanediol, even more preferably bio-1,3-butanediol, deriving from biosynthesis processes. Preferably, said 1,3-butadiene is bio-1,3-butadiene.

It is known that the industrial production of 1,3-butanediol, 1,3-butadiene and alkenols, is currently based on classical petrochemical processes.

Diols having four carbon atoms, in general, and 1,3-butanediol (also generally indicated as 1,3-BDO) in particular, are, in fact, generally obtained by means of complex petrochemical processes as described, for example, by Gräfje H. et al. in "Butanediols, Butenediol, and Butynediol", *Ulmann's Encyclopedia of Industrial Chemistry* (2000). In particular, 1,3-butanediol is produced via acetaldehyde, hydroxy-butyraldehyde and subsequent reduction, and is generally used as a resin component or as a solvent.

Processes for the production of alkenols are also known in the art.

U.S. Pat. No. 5,406,007, for example, describes a process for the preparation of an allylic alcohol, a homoallylic alcohol, or a mixture thereof, which comprises hydrogenating an epoxyalkene, wherein the epoxy group and the ethylene insaturation are conjugated, in the presence of a nickel catalyst modified with sulfur or sulfided, operating under typical hydrogenation temperature and pressure conditions. Said process is preferably useful for the preparation of a mixture of 2-buten-1-ol (crotyl alcohol) and 3-buten-1-ol.

U.S. Pat. No. 6,278,031 describes a process for the preparation of 2-buten-1-ol compounds having formula (I):

wherein the radicals $R^1$, $R^2$, $R^3$, $R^4$, $R^5$ and $R^6$, are, each independently, hydrogen or an aliphatic radical optionally substituted with an OH, or with an OR group wherein R is an aliphatic group, a halogen or a carboxyl group, $R^2$ moreover represents a —CHO radical, or $R^2$ and $R^5$ together with the carbon atoms positioned between them form an alicyclic ring, and $R^6$, in addition, represents a cycloaliphatic, araliphatic, aromatic radical or a —C(=O)—$R^7$ radical wherein $R^7$ is an aliphatic, cycloaliphatic, araliphatic or aromatic radical, said process comprising isomerising 3-buten-1-ol compounds having formula (II):

wherein the radicals $R^1$, $R^2$, $R^3$, $R^4$, $R^5$ and $R^6$, have the same meanings described above, in the presence of hydrogen and a catalyst, wherein the process is carried out in continuous on a fixed-bed catalyst, wherein the catalyst comprises palladium and selenium or tellurium or a mixture of selenium and tellurium on a silicon dioxide carrier, and has a BET surface area ranging from 80 $m^2/g$ to 380 $m^2/g$ and a pore volume ranging from 0.6 $cm^3/g$ to 0.95 $cm^3/g$ within a pore diameter ranging from 3 nm to 300 μm, from 80% to 95% of the pore volume being within a pore diameter ranging from 10 nm to 100 nm.

Alternatively, 2-buten-1-ol (crotyl alcohol) can be prepared by the reduction of crotonaldehyde as described, for example, in "Merck Index" (1976), 9th Edition. Furthermore, 2-buten-1-ol (crotyl alcohol) can be prepared by means of biosynthesis processes as described, for example, in international patent application WO 2013/130481 (as intermediate in the synthesis of 1,3-butadiene), or in American patent application US 2013/109064.

U.S. Pat. No. 4,400,562 describes a method for synthesizing an alkenol from 1,3-butanediol in liquid phase which comprises: mixing a sulfate of a trivalent metal selected from aluminium sulfate, chromium sulfate, iron sulfate, and mixtures thereof, as catalyst, with 1,3-butanediol, in an effective quantity, obtaining a mixture of said catalyst suspended in 1,3-butanediol; heating said mixture to a temperature ranging from about 70° C. below to about 100° C. above the boiling point of 1,3-butanediol, obtaining a partial dehydration of the 1,3-butanediol to 3-buten-1-ol which evaporates from the reaction mixture; and condensing said vapour so as to isolate the 3-buten-1-ol.

Alternatively, 3-buten-1-ol can be prepared from propylene and formaldehyde, in the presence of a catalyst, operating at high temperatures, as described, for example, in American patent application US 2013/109064.

3-Buten-2-ol (methylvinylcarbinol) and butadiene can be obtained by the dehydration of 2,3-butanediol in the presence of thorium oxide as described, for example, by Winfield M. E. in "The catalytic Dehydration of 2,3-butanediol to Butadiene. II. Adsorption Equilibria", *Australian Journal of Scientific Research* (1950), Vol. 3(2), pages 290-305.

Alternatively, 3-buten-2-ol (methylvinylcarbinol), alone or in a mixture with other butenols, can be obtained, for example: by the thermal decomposition of polyols or derivatives thereof (e.g., 1,3-butyleneglycoldiacetate) as described, for example, in German patent DE 1,150,671; or by the reduction of acetylenes or unsaturated carbonyl compounds as described, for example, in Russian patent SU 396312 or in Japanese patent application JP 63/222135.

2-buten-1-ol (crotyl alcohol) can be used, for example, as precursor of halides, crotyl esters or crotyl ethers which, in turn, can be used, for example, as intermediates in the production of monomers, in fine chemistry (for example, for the production of sorbic acid, trimethylhydroquinone, crotonic acid, 3-methoxybutanol), in agricultural chemistry, in pharmaceutical chemistry.

3-buten-1-ol (allylcarbinol) can be used, for example, as raw material in pharmaceutical chemistry, in agricultural chemistry, in perfumes, in resins. Aryl-substituted aldehydes are obtained, for example, from the coupling reaction of 3-buten-1-ol (allylcarbinol) with aryl halides, catalyzed by palladium, which can be used in pharmaceutical chemistry, for example, as antifolates.

3-buten-2-ol (methylvinylcarbinol) can be used as solvent, in fine chemistry, as component in the modification of polymers such as, for example, polyolefins (as described, for example, in German patent DE 1,908,620).

The above alkenols can also be used for the production of 1,3-butadiene.

1,3-butadiene is a fundamental product of petrochemistry. About ten million tons of 1,3-butadiene are produced each year and preferably used in the production of various products such as, for example, synthetic rubbers, resins, acrylonitrile-butadiene-styrene (ABS) terpolymers, hexamethylenediamine, butanediols, in particular, 1,4-butanediol. More than 95% of 1,3-butadiene produced each year is a by-product deriving from steam cracking processes for the production of ethylene and other olefins and is separated by means of extractive distillation. Among the "on-purpose" production processes of 1,3-butadiene, the dehydrogenation of butane and/or butenes can be mentioned, for example.

The possibility of developing alternative, efficient and high-productivity production processes of 1,3-butadiene, with reduced production costs and a reduced environmental impact, is still of great interest. In particular, new processes capable of using materials deriving from biosynthesis processes, for example bio-alkenols, in particular bio-alkenols deriving from the catalytic dehydration of bio-1,3-butanediol, to give, via a further catalytic dehydration, bio-1,3-butadiene, are still of great interest.

Renewable sources, biomasses, syngas, or other gaseous carbon sources are preferably used as carbon sources in said biosynthesis processes.

Syngas can be obtained through processes known in the art by the gasification of materials containing carbon (such as, for example, coal, biomasses, waste-products, natural gas, and the like).

Said biosynthesis processes are generally carried out by microorganisms that are capable of using carbon sources such as, for example, carbohydrates. For example, among the carbohydrate sources, sugars (glucose, xylose, arabinose, fructose, and the like), biomasses (cellulose, hemicellulose, lignin, and the like), preferably containing carbohydrates, other renewable sources, can be mentioned.

The production of 1,3-butadiene from diols is known in the art, but the approaches that have found industrial applications, even if in particular and/or unconventional contexts, are those based on technologies of the Reppe type that use catalysts based on phosphates: in this respect, reference can be made to the article of Bender M., "An Overview of Industrial Processes for the Production of Olefins—$C_4$ Hydrocarbons", "*ChemBioEng Reviews*" (2014), Vol. 1, No. 4, pages 136-147 (DOI: 10.1002/cben.201400016). Said approaches, however, are not considered nowadays as being industrializable due to the low productivities, to the particular reaction conditions used and to the quick decay of the catalysts used, as is evident, for example, from the documents cited hereunder.

U.S. Pat. No. 2,310,809 describes a method for the production of diolefins, in particular 1,3-butadiene, by the catalytic dehydration of aliphatic glycols having at least four carbon atoms, which comprises putting said glycols in vapour form, preferably in the presence of steam or of other diluent gases, in contact with a dehydration catalyst selected from compounds containing phosphorous, capable of operating at high temperatures. The above process is said to increase the yield of diolefins, reduce the formation of by-products and maintain the life of the catalyst for a long period of time (in particular, Example 1 and Example 2 indicate a yield of 1,3-butadiene starting from 1,3-butanediolo, equal to 85% and 90%, respectively). The above process, however, is difficult to apply industrially as extremely low feeding rates are used (equal to 0.060 kg×$h^{-1}$×$l^{-1}$, 60 parts of 1,3-butanediol and 40 parts of water, in the presence of n-hexane, in Example 1; and equal to 0.060 kg×$h^{-1}$×$l^{-1}$, 40 parts of 1,3-butanediol, 40 parts of water and 20 parts of 1,4-butanediol, in the presence of tetrahydrofuran, in Example 2), with consequent low productivities of the catalyst. Furthermore, organic substances, liquid under normal conditions, for example n-hexane, are used, which are vaporized on the catalyst in order to improve its stability.

U.S. Pat. No. 2,237,866 describes a process for the preparation of diolefins, in particular, 1,3-butadiene, through the catalytic dehydration of glycols and the corresponding alcohols, in the presence of a catalyst selected from substances containing phosphorous in vapour phase (for example, esters of acids containing phosphorous, phosphorous oxychloride, phosphorous trichloride, phosphorous pentachloride).

U.S. Pat. No. 2,426,678 describes a method for regenerating dehydration catalysts based on phosphates, preferably ammonium phosphate, using volatile esters of phosphoric acid, and ammonia ($NH_3$).

German patent DD 132126 describes the dehydration of 1,3-butanediol to 1,3-butadiene with yields of about 90%, but with extremely low productivities and low feeding rates (equal to 0.0375 kg×$h^{-1}$×$l^{-1}$ in Example 2).

Other approaches have not produced better results. Studies, for example, on the reactivity of 2-buten-1-ol (crotyl alcohol) and of 3-buten-2-ol (methylvinylcarbinol) to give 1,3-butadiene using catalysts such as bismuth molybdate, in an oxidizing environment, are described by Adams C. R, in "Exploratory catalytic oxidations with bismuth molibdate", "*Journal of catalysis*" (1968), Vol. 10, pages 355-361). Bismuth molybdate, however, is considered as being a catalyst having a low selectivity for the dehydration of 1,3-butanediol to 1,3-butadiene via 2-buten-1-ol (crotyl alcohol) as indicated, for example, by Adams C. R., in "Selectivity Effects in Some Catalytic Oxidation Processes", "*Industrial & Engineering Chemistry*" (1969), Vol. 61 (6), pages 30-38 (DOI: 10.1021/ie50714a006).

Studies relating to the reactivity of alkenols to conjugated dienes different from 1,3-butadiene are also known.

U.S. Pat. No. 3,714,285, for example, describes a process for the preparation of isoprene through the catalytic dehydration of 3-methyl-3-buten-1-ol (methylbutenol) which comprises putting said 3-methyl-3-buten-1-ol (methylbutenol) in contact, at high temperatures, with an acid catalyst such as phosphoric acid supported on pumice.

The disadvantages relating to the use of catalysts based on supported phosphoric acid that require the replacement of the phosphoric acid lost during the reaction, are, however, well known. These problems are also known in other contexts, such as, for example alkylations of aromatic compounds as described, for example, in American patent application US 2005/075239, which points out that these catalysts create problems relating to environmental impact and safety due to corrosion and to the disposal of the exhausted catalyst.

The use of different dehydration catalysts is also known in the art.

Weissermel K., Arpe H. J. in "*Industrial Organic Chemistry*" (2008), $3^{th}$ Ed., John Wiley & Sons, pages 117, for example, describe the Snamprogetti process for the production of isoprene from acetone-acetylene, used in Italy up until the eighties, in the presence of alumina ($Al_2O_3$).

British patent GB 935631 describes a process for the preparation of isoprene through the catalytic dehydration of 3-methyl-3-buten-1-ol (methylbutenol), in vapour phase, in the presence of a catalyst that essentially consists of alumina ($Al_2O_3$) having a surface area greater than 200 $m^2$/g, at a temperature ranging from 260° C. to 270° C., for a time ranging from 1 second to 5 seconds.

The use of silica-aluminas ($SiO_2$—$Al_2O_3$) as catalysts in the production of 1,3-butadiene from alkenols is also known, as described, for example, by Sato S. et al., in "Catalytic reaction of 1,3-butanediol over solid catalyst", "*Journal of Molecular Catalysis A: Chemical*" (2006), Vol. 256, pages 106-112. In particular, Table 5 indicates conversion and selectivity values to 1,3-butadiene obtained for 3-buten-1-ol, 2-buten-1-ol and 3-buten-2-ol, in the presence of a silica-alumina ($SiO_2$—$Al_2O_3$) as catalyst, operating at 250° C. The values obtained are the following:

conversion 3-buten-1-ol=41.5%; selectivity to 1,3-butadiene=12.8%;

conversion 2-buten-1-ol=76.7%; selectivity to 1,3-butadiene=92.8%;

conversion 3-buten-2-ol=70.8%; selectivity to 1,3-butadiene=93.0%.

The silica-alumina ($SiO_2$—$Al_2O_3$) used by Sato S. et al., is the product known with the trade-name N631-L of Nikki Chemical, and has a surface area equal to 420 $m^2$/g and a Si/Al ratio equal to 5.4, corresponding to an alumina content ($Al_2O_3$) of about 13% (as described, in Example 1 of U.S. Pat. No. 3,689,477 and by Uemichi Y. et al., in "Chemical recycling of poly(ethylene) by catalytic degradation into aromatic hydrocarbons using H-Ga-silicate", "*Chemical communications*" (1998), 1975-1976 DOI: 10.1039/A804927K).

None of the documents indicated above, however, allow useful teachings to be obtained for use in industrial applications as they provide purely specific data, they do not face the problem of the decay of the catalyst, they indicate low conversions (lower than 80%), they use ideal feeds obtained from the use of commercial alkenols and not deriving from a previous dehydration reaction (for example, from the catalytic dehydration of a diol to give alkenols).

Analogous conclusions can be made from consulting recent reviews, such as, for example, that of Makshina E. V. et al., "Review of old chemistry and new catalytic advances in the on-purpose synthesis of butadiene", "*Chemical Society Review*" (2014), Vol. 43, pages 7917-7953 (DOI: 10.1039/C4CS00105B).

International patent application WO 2013/130481 describes a process for the preparation of 1,3-butadiene by putting 2-buten-1-ol (crotyl alcohol) produced from a recombinant host cell described therein, in contact with a solid acid catalyst selected, for example, from silica-aluminas ($SiO_2$—$Al_2O_3$), under suitable operating conditions. Also in this case, however, there are no teachings relating to specific catalysts and/or specific modes of use of said catalysts.

Furthermore, from what is reported above, it is evident that there is little information on the deactivation of acid catalysts in the dehydration of alkenols. In this respect, it should be remembered that it is known that the dehydration of alcohols can take place by means of an acid catalysis and the main product obtained is the olefin having a number of carbon atoms corresponding to the starting alcohol, or the ether of said alcohol, but that, in addition to said main reactions, there can also be secondary reactions such as, for example, dehydrogenation and/or oligomerization of the olefins and/or cracking phenomena. By-products are obtained from said secondary reactions, which lead to a deactivation of the dehydration catalyst as described, for example, by Bartholomew C. H., in "Mechanisms of catalyst deactivation" (2001), "*Applied Catalysis A: General*" Vol. 212, pages 17-60.

An optimization of the catalytic system and of the reaction conditions is the approach generally followed for limiting processes that lead to the deactivation of the catalyst as described, for example, by Moulijn J. A. et al., in "Catalyst deactivation: is it predictable? What to do?", "*Applied Catalysis A: General*" (2001), Vol. 212, pages 3-16.

Finding a process in which an alkenol, more preferably a butenol, even more preferably bio-butenol deriving from biosynthesis processes or from precursors obtained by means of biosynthesis processes, is subjected to dehydration obtaining 1,3-butadiene, in particular bio-1,3-butadiene, is consequently of great interest.

The Applicant has therefore considered the problem of finding a process for the production of dienes, in particular conjugated dienes, more specifically 1,3-butadiene, even more specifically bio-1,3-butadiene, by the dehydration of at least one alkenol, in particular at least one alkenol deriving from biosynthesis processes, which is capable of overcoming the drawbacks indicated above and capable of giving high quantities of dienes, in particular conjugated dienes, more specifically 1,3-butadiene, even more specifically bio-1,3-butadiene.

The Applicant has now found that the use of a catalytic material comprising at least one acid catalyst based on silica ($SiO_2$) and alumina ($Al_2O_3$), in particular a silica-alumina ($SiO_2$—$Al_2O_3$) having a content of alumina ($Al_2O_3$) lower than or equal to 12% by weight with respect to the total weight of said catalyst, in the above process for the production of dienes, in particular conjugated dienes, more specifically 1,3-butadiene, even more specifically bio-1,3-butadiene, is capable of overcoming the drawbacks described above.

Numerous advantages are obtained with the use of the above catalytic material. Said catalytic material, for example, allows high conversion and selectivity values to be obtained. Furthermore, said catalytic material has high lifetimes, also operating at alkenol:diluent ratios included within a wide range. Said advantages also remain when operating within a wide range of operating conditions, i.e. at different temperatures, at different contact times ($\tau$), and allow various mixtures of alkenols to be used, i.e. both mixtures of commercial alkenols and mixtures of alkenols deriving from previous dehydration processes or directly from biosynthesis processes. Furthermore, said catalytic material can be subjected to regeneration and used again in the above process for the production of dienes with excellent results.

An object of the present invention therefore relates to a process for the production of a diene, preferably a conjugated diene, more preferably 1,3-butadiene, comprising the dehydration of at least one alkenol in the presence of at least one catalytic material comprising at least one acid catalyst based on silica ($SiO_2$) and alumina ($Al_2O_3$), preferably a silica-alumina ($SiO_2$—$Al_2O_3$), said catalyst having a content of alumina lower than or equal to 12% by weight, preferably ranging from 0.1% by weight to 10% by weight, with respect to the total weight of the catalyst.

For the purpose of the present description and of the following claims, the definitions of the numerical ranges always comprise the extremes unless otherwise specified.

For the purpose of the present description and of the following claims, the term "comprising" also includes the terms "which essentially consists of" or "which consists of".

For the purpose of the present description and of the following claims, the term "having a content of alumina lower than or equal to 12% by weight", means that said acid catalyst based on silica ($SiO_2$) and alumina ($Al_2O_3$) may not contain alumina ($Al_2O_3$), i.e. it may contain 0% of alumina ($Al_2O_3$), or it refers to a catalyst selected from acid catalysts based on silica ($SiO_2$) and alumina ($Al_2O_3$) known as "All Silica" forms.

In this respect, it should be remembered that "All Silica" forms are similarly considered as extremes of composition of different silico-aluminates. "All Silica" forms of zeolites (which are silico-aluminates) are known, for example, to skilled persons in the field of catalysis, such as Silicalite-1 and Silicalite-2 that are "All Silica" forms of ZSM-5 and ZSM-11 zeolites.

According to a preferred embodiment of the present invention, said alkenol can be selected, for example, from: 3-buten-2-ol (methylvinylcarbinol—CAS Number 598-32-3), 3-buten-1-ol (allylcarbinol—CAS Number 627-27-0), 2-buten-1-ol (crotyl alcohol), or mixtures thereof, preferably from 2-buten-1-ol (crotyl alcohol), 3-buten-2-ol (methylvinylcarbinol—CAS Number 598-32-3), or mixtures thereof.

For the purpose of the present description and of the following claims, the term 2-buten-1-ol (crotyl alcohol) refers to: both the mixture of cis and trans isomers, and the cis isomer as such (CAS Number 4088-60-2), and the trans isomer as such (CAS Number 504-61-0).

According to a preferred embodiment of the present invention, said alkenol can be obtained directly from biosynthesis processes, or by catalytic dehydration processes of at least one diol, preferably a butanediol, more preferably 1,3-butanediol, even more preferably bio-1,3-butanediol, deriving from biosynthesis processes.

Biosynthesis processes capable of directly giving alkenols are described, for example, in international patent application WO 2013/130481, or in American patent application US 2013/109064, indicated above.

For the purpose of the present invention, said alkenol can be obtained by the catalytic dehydration of at least one diol, preferably at least one butanediol, more preferably 1,3-butanediol, even more preferably bio-1,3-butanediol, deriving from biosynthesis processes, in the presence of at least one catalyst based on cerium oxide, wherein said catalyst based on cerium oxide is obtained by precipitation, in the presence of at least one base, of at least one compound containing cerium. Further details relating to said process can be found in Italian patent application MI2014A000897 in the name of the Applicant and incorporated herein as reference.

According to a particularly preferred embodiment of the present invention, said alkenol derives from the catalytic dehydration of at least one diol, preferably a butanediol, more preferably 1,3-butanediol, even more preferably bio-1,3-butanediol, deriving from the fermentation of sugars, preferably from the fermentation of sugars deriving from biomass.

For the purpose of the present description and of the following claims, the term the term "biomass" indicates any organic material of a vegetable origin including: products deriving from agriculture such as, for example, guayule, thistle, corn, soybean, cotton, linseed, rapeseeds, sugar cane, palm, including scraps, residues and waste products deriving from said products or from their processing; products deriving from crops specifically cultivated for energy purpose, such as, for example, *miscanthus*, foxtail millet, common cane, comprising scraps, residues and waste products deriving from said products or from their processing; products deriving from forestation or silviculture including scraps, residues and waste products deriving from said products or from their processing; scraps of agro-food products destined for human nutrition or zootechnics; residues from the paper industry; waste products coming from the differentiated collection of solid urban waste, such as, for example, urban waste of a vegetable origin, paper.

Said diol is preferably bio-1,3-butanediol deriving from the fermentation of sugars obtained from guayule or thistle, including scraps, residues, waste products deriving from said guayule and/or thistle or from their processing.

Even more preferably, said diol is bio-1,3-butanediol deriving from the fermentation of sugars obtained from guayule, including scraps, residues, waste products deriving from said guayule or from its processing.

In the case of the use of a biomass of a vegetable origin, for producing sugars, said biomass is subjected to physical treatment (for example, extrusion, steam explosion, and the like) and/or to chemical hydrolysis and/or to enzymatic hydrolysis, obtaining mixtures of carbohydrates, aromatic compounds and other products deriving from cellulose, hemicellulose and lignin present in the biomass. In particular, the carbohydrates obtained are mixtures of sugars with 5 or carbon atoms including, for example, sucrose, glucose, xylose, arabinose, galactose, mannose and fructose, to be used in the fermentation. Processes for the production of sugars from biomass are described in the art such as, for example, in Italian patent application MI2013A002069, in the name of the Applicant. Said fermentation is generally carried out by microorganisms, in particular genetically modified microorganisms, capable of producing the alcohols of interest. Further details relating to processes for the synthesis of 1,3-butanediol, in particular bio-1,3-butanediol, starting from renewable sources can be found, for example, in American patent applications US 2010/330635, US 2012/329113 and US 2013/109064.

If the diol derives from biosynthesis processes, for example, from the fermentation of sugars, the aqueous mixture of alkenols obtained can be subjected to separation processes known in the art such as, for example, total or partial distillation. Alternatively, said aqueous mixture of alkenols can be used as such, using, in fact, water as diluent, without the necessity of subjecting said aqueous mixture to costly elimination processes of the water or, in any case, limiting said elimination.

It should be noted out that if said alkenol derives from the catalytic dehydration of at least one diol, the dehydration of said at least one diol to give at least one alkenol and the subsequent dehydration of said at least one alkenol to give a diene, can be carried out:

in the same reactor or in different reactors, preferably in different reactors;

in continuous or batchwise, preferably batchwise.

For the purpose of the present invention, said acid catalyst based on silica ($SiO_2$) and alumina ($Al_2O_3$), can be obtained by means of processes known in the art and can be used in various forms. Said acid catalyst based on silica ($SiO_2$) and alumina ($Al_2O_3$) can be used, for example, as such, or it can be bound and/or formed operating according to any process known in the art. Further details relating to said processes can be found, for example, in U.S. Pat. No. 3,974,099, U.S. Pat. No. 4,226,743, U.S. Pat. No. 6,451,200, U.S. Pat. No. 4,499,197, U.S. Pat. No. 4,175,118, U.S. Pat. No. 5,045,519, U.S. Pat. No. 6,642,172; or in: Campanati M. et al., "Fundamentals in the preparation of heterogeneous catalysts", "*Catalysis Today*" (2003), Vol. 77, pages 299-314; Haber J. et al., "Manual of methods and procedures for catalyst characterization", "*Pure & Applied Chemistry*" (1995), Vol. 67, No. 8-9, pages 1257-1306.

According to a preferred embodiment of the present invention, said acid catalyst based on silica ($SiO_2$) and alumina ($Al_2O_3$) can be obtained by means of incipient wetness impregnation, wherein the volume of a solution of a metal (for example, aluminium) having an appropriate concentration is equal to or slightly lower than that of the pore volume of a solid carrier (for example, silica).

According to a further preferred embodiment of the present invention, said acid catalyst based on silica ($SiO_2$) and alumina ($Al_2O_3$) can be obtained by means of a process comprising:

- preparing a solution or suspension of alumina ($Al_2O_3$), or its precursors, that can be selected, for example, from: aluminium alkoxides (for example, aluminium tri-sec-butoxide), soluble aluminium salts (for example, aluminium sulfate), aluminates (for example, sodium aluminate);
- adding to said solution or suspension of alumina ($Al_2O_3$), or its precursors, a solution or suspension of silica ($SiO_2$), or its precursors, that can be selected, for example, from: silicic acid (for example, orthosilicic acid), alkali metal silicates (for example, sodium silicate);
- recovering the solid obtained by means of precipitation, or gelation, and subjecting it, optionally:
- to an ion-exchange step in the presence of at least one compound capable of exchanging ions with the surface of the solid obtained, that can be selected, for example, from aqueous solutions of salts containing ammonium ions (for example, ammonium acetate, ammonium nitrate, ammonium sulfate); and/or
- to a binding step in the presence of at least one precursor of silica ($SiO_2$) that can be selected, for example, from colloidal silicas (for example, Ludox® TMA—Sigma-Aldrich), silica alkoxides (for example, tetraethylorthosilicate); or of at least one precursor of alumina ($Al_2O_3$) that can be selected, for example, from bohemite or pseudo-bohemite (for example, Versal™ V-250—UOP); and/or
- to a forming step such as, for example, extrusion, spherulization, tabletting, granulation;
- subjecting it to optional thermal and/or to optional calcination treatment, said optional thermal and/or optional calcination treatment being carried out before or after one of the above steps, i.e. ion exchange, and/or binding, and/or forming.

It should be noted that, for the purpose of the present invention, said solution or suspension of alumina ($Al_2O_3$), or its precursors, can be added in one or more steps to said solution or suspension of silica ($SiO_2$), or its precursors.

It should also be noted that, for the purpose of the present invention, said solution or suspension of silica ($SiO_2$), or its precursors, can be added in one or more steps to said solution or suspension of alumina ($Al_2O_3$), or its precursors.

The additions described above can be carried out by means of methods known in the art, and also referring to current laboratory practices (for illustrative and non-limiting purpose of the present invention, by weighing, by volumetric dosages, etc.). There can, in any case, be more than two addition steps without, however, create any critical aspect and, therefore, a limitation of the present invention.

For the purpose of the present invention, said solution or suspension of alumina ($Al_2O_3$), or its precursors, can comprise from 5% by weight to 70% by weight, preferably from 10% by weight to 60% by weight, even more preferably from 15% by weight to 50% by weight, with respect to the total weight of said solution or suspension, of alumina ($Al_2O_3$), or at least one of its precursors.

Alternatively, said solution or suspension of alumina ($Al_2O_3$), or its precursors, can be a hydro-alcohol solution comprising from 5% by weight to 95% by weight, preferably from 15% by weight to 60% by weight, even more preferably from 10% by weight to 30% by weight, with respect to the total weight of said hydro-alcohol solution, of at least one alcohol selected, for example, from ethanol, 2-methoxyethanol, n-propanol, iso-propanol, n-butanol, iso-butanol, tert-butanol, or mixtures thereof.

For the purpose of the present invention, said solution or suspension of silica ($SiO_2$), or its precursors, can comprise from 5% by weight to 70% by weight, preferably from 10% by weight to 60% by weight, even more preferably from 15% by weight to 50% by weight, with respect to the total weight of said solution or suspension, of silica ($SiO_2$), or at least one of its precursors.

Alternatively, said solution or suspension of silica ($SiO_2$), or its precursors, can be a hydro-alcohol solution comprising from 5% by weight to 95% by weight, preferably from 15% by weight to 60% by weight, even more preferably from 10% by weight to 30% by weight, with respect to the total weight of said hydro-alcohol solution, of at least one alcohol selected, for example, from ethanol, 2-methoxyethanol, n-propanol, iso-propanol, n-butanol, iso-butanol, tert-butanol, or mixtures thereof.

The solid obtained from the above process can be recovered through processes known in the art such as, for example, filtration, decanting, and the like.

The above optional thermal treatment can be carried out at a temperature ranging from 100° C. to 200° C., preferably ranging from 105° C. to 150° C., for a time ranging from 2 hours to 72 hours, preferably ranging from 3 hours to 18 hours.

The above optional calcination can be carried out at a temperature ranging from 150° C. to 1500° C., preferably ranging from 200° C. to 1400° C., even more preferably ranging from 300° C. to 1200° C., for a time ranging from 1 hour to 24 hours, preferably ranging from 2 hours to 10 hours, even more preferably ranging from 4 hours to 8 hours. Said calcination can generally be carried out in air, or in the presence of an inert gas [for example, nitrogen ($N_2$)], or in a controlled atmosphere (oxidizing or reducing), preferably in air.

As indicated above, the acid catalyst based on silica ($SiO_2$) and alumina ($Al_2O_3$), can be used in various forms. Said catalyst can be used, for example, as such, or it can be formed, operating according to any forming process known in the art such as, for example, extrusion, spherulization, tabletting, granulation, and the like. The optional thermal treatment and optional calcination indicated above can be carried out before or after one of said forming processes.

Preferably, said acid catalyst based on silica ($SiO_2$) and alumina ($Al_2O_3$), can be used in extruded form, optionally containing traditional binders such as, for example, alumina ($Al_2O_3$), silica ($SiO_2$), zirconium oxide, titanium oxide, preferably silica ($SiO_2$) or alumina ($Al_2O_3$), even more preferably alumina ($Al_2O_3$).

If said traditional binders are present, the extrusion generally also envisages the use of a peptizing agent such as, for example, aqueous solutions of acetic acid, of nitric acid, or of ammonium hydroxide, that can be mixed with the catalyst and binder before the extrusion, until a homogeneous paste is obtained. At the end of said extrusion, the pellets obtained are generally subjected to calcination operating as described above.

The solid obtained after binding and/or forming can contain from 5% by weight to 90% by weight, preferably from 10% by weight to 75% by weight, more preferably from 20% by weight to 55% by weight, of binder, with respect to the total weight of said acid catalyst based on silica ($SiO_2$) and alumina ($Al_2O_3$).

Said acid catalyst based on silica (SiO$_2$) and alumina (Al$_2$O$_3$) can also be used in extruded form, optionally supported on preformed carriers such as, for example, silicas, aluminas, and the like.

According to a preferred embodiment of the present invention, said acid catalyst based on silica (SiO$_2$) and alumina (Al$_2$O$_3$) can have a specific surface area ranging from 50 m$^2$/g to 800 m$^2$/g, preferably ranging from 150 m$^2$/g to 700 m$^2$/g, even more preferably ranging from 200 m$^2$/g to 600 m$^2$/g.

According to a preferred embodiment of the present invention, said catalytic material comprises at least one acid catalyst based on silica (SiO$_2$) and alumina (Al$_2$O$_3$) and at least one binder that can be selected, for example, from alumina (Al$_2$O$_3$), silica (SiO$_2$), zirconium oxide, titanium oxide, preferably silica (SiO$_2$) or alumina (Al$_2$O$_3$), even more preferably alumina (Al$_2$O$_3$).

According to a further preferred embodiment of the present invention, said catalytic material comprising at least one acid catalyst based on silica (SiO$_2$) and alumina (Al$_2$O$_3$), and at least one binder selected from alumina (Al$_2$O$_3$) or silica (SiO$_2$), and/or subjected to forming, can have a specific surface area ranging from 25 m$^2$/g to 700 m$^2$/g, preferably ranging from 100 m$^2$/g to 600 m$^2$/g, even more preferably ranging from 150 m$^2$/g to 500 m$^2$/g.

For the purpose of the present description and of the following claims, the term "specific surface area" indicates the BET specific surface area determined by static nitrogen (N$_2$) absorption, at a temperature of the liquid nitrogen equal to −196.15° C. (77 K), with an ASAP instrument of Micromeritics, in accordance with standard ASTM D3663-03 (2008).

The elemental analysis of said acid catalyst based on silica (SiO$_2$) and alumina (Al$_2$O$_3$) was carried out via WD-XRF (Wavelength Dispersion X-Ray Fluorescence), with a PANalytical Axios Advanced spectrometer equipped with a 4 KW X-ray tube with a rhodium (Rh) anode.

According to a preferred embodiment of the present invention, said process for the production of a diene can be carried out in the presence of at least one diluent that can be selected, for example, from: inert gases such as, for example, nitrogen (N$_2$), argon (Ar), preferably nitrogen (N$_2$); or from compounds having a boiling temperature higher than or equal to 50° C. and a melting temperature lower than or equal to 40° C., which are preferably in the liquid state at room temperature (25° C.) and at atmospheric pressure (1 atm), such as, for example, water, tetrahydrofuran, cyclohexane, benzene. Nitrogen (N$_2$), water, are preferred, water is particularly preferred.

According to a preferred embodiment of the present invention, said process for the production of dienes can be carried out, if the diluent is selected from inert gases, at a molar ratio between diluent and alkenol(s) higher than 0.3, preferably ranging from 0.5 to 2.

According to a preferred embodiment of the present invention, said process for the production of a diene can be carried out, if the diluent is selected from compounds having a boiling temperature higher than or equal to 50° C. and a melting temperature lower than or equal to 40° C., which are preferably in the liquid state at room temperature (25° C.) and at atmospheric pressure (1 atm), at a molar ratio between diluent and alkenol(s) ranging from 0.01 to 100, preferably ranging from 0.1 to 50, more preferably ranging from 1 to 10.

According to a preferred embodiment of the present invention, said process for the production of a diene can be carried out at a temperature ranging from 150° C. to 500° C., preferably ranging from 200° C. to 450° C., more preferably ranging from 250° C. to 400° C.

According to a preferred embodiment of the present invention, said process for the production of a diene can be carried out at a pressure ranging from 0.05 bara (absolute bar) to 50 bara (absolute bar), preferably ranging from 0.3 absolute bar to 3.5 bara (absolute bar), more preferably ranging from 0.8 bara (absolute bar) to 2.5 bara (absolute bar).

According to a preferred embodiment of the present invention, said process for the production of a diene can be carried out operating at a contact time (t), calculated as ratio of the volume of catalytic material charged with respect to the volumetric feeding flow-rate, ranging from 0.01 seconds to 10 seconds, preferably ranging from 0.05 seconds to 8 seconds, more preferably ranging from 0.1 seconds to 4 seconds.

According to a preferred embodiment of the present invention, said catalytic material based on silica-alumina can be pre-treated at the temperature at which said process for the production of a diene is carried out, i.e. at a temperature ranging from 150° C. to 500° C., preferably ranging from 200° C. to 450° C., more preferably ranging from 250° C. to 400° C., preferably in the presence of at least one diluent selected from those indicated above, more preferably in the presence of water.

For the purpose of the present invention, said process for the production of a diene can be carried out in gas phase or in mixed liquid/gas phase, preferably in gas phase, batch-wise (for example, in a stirred and heated autoclave), or in continuous (for example, in one or more catalytic reactors in series), preferably in continuous. Said reactors can be fixed-bed reactors or fluid-bed reactors, preferably fixed-bed reactors. If the reactors are fixed-bed reactors, the catalytic material can be distributed on several beds. Said reactors can envisage a recycling of part of the reaction effluents or of the catalytic material by configuring a recirculated reactor. If a liquid phase is present, the process for the production of dienes can be carried out in continuous stirred reactors, containing the catalytic material in dispersion.

Some illustrative and non-limiting examples are provided for a better understanding of the present invention and for its practical embodiment.

EXAMPLE 1

Preparation of a Silica-Alumina (SiO$_2$—Al$_2$O$_3$) Having a Content of Alumina (Al$_2$O$_3$) Equal to 0%, with an Alumina (Al$_2$O$_3$) Binder 7.6 g of tri-sec-butanol (Aldrich) were introduced into a first 500 ml flask. 50 g of orthosilicic acid (Aldrich, <20 mesh), as silica precursor (SiO$_2$), and 250 g of demineralized water were introduced into a second 500 ml flask: the suspension of orthosilicic acid obtained was slowly added (10 minutes) to said first flask and the whole mixture was maintained at room temperature (25° C.), under vigorous stirring (500 rpm), for about 2 hours. The suspension obtained was then heated to 90° C., and kept at this temperature, under vigorous stirring (500 rpm), for about 1 hour. After cooling to room temperature (25° C.), the suspension obtained was filtered, the solid obtained was washed with 5 liters of demineralized water, dried at 120° C. for a night and subsequently calcined at 500° C. for 5 hours obtaining a silica-alumina (SiO$_2$—Al$_2$O$_3$) in the form of a colourless powder (46 g), having a BET specific surface area, determined as described above, equal to 479 m$^2$/g.

A part of said silica-alumina ($SiO_2$—$Al_2O_3$), 20.5 g, was mixed with 11.4 g of pseudo-bohemite Versal™ V-250 (UOP), as alumina precursor ($Al_2O_3$) of the binder, and 300 ml of a solution at 4% of acetic acid (Aldrich) in a 800 ml beaker. The mixture obtained was kept under vigorous stirring (500 rpm), at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina ($SiO_2$—$Al_2O_3$) with an alumina binder ($Al_2O_3$), in the form of a colourless solid (24 g) which was subsequently granulated mechanically and the fraction of granules having dimensions ranging from 0.5 mm to 1 mm was used as catalytic material. Said silica-alumina ($SiO_2$—$Al_2O_3$) with an alumina binder ($Al_2O_3$) had a BET specific surface area, determined as described above, equal to 389 m²/g.

EXAMPLE 2

Preparation of a Silica-Alumina ($SiO_2$—$Al_2O_3$) Having a Content of Alumina ($Al_2O_3$) Equal to 3.8%, with an Alumina ($Al_2O_3$) Binder 7.6 g of aluminium tri-sec-butoxide (Aldrich), as alumina precursor ($Al_2O_3$), were introduced into a first 500 ml flask. 50 g of orthosilicic acid (Aldrich, <20 mesh), as silica precursor ($SiO_2$), and 250 g of demineralized water were introduced into a second 500 ml flask: the suspension of orthosilicic acid obtained was slowly added (10 minutes) to said first flask and the whole mixture was maintained at room temperature (25° C.), under vigorous stirring (500 rpm), for about 2 hours. The suspension obtained was then heated to 90° C., and kept at this temperature, under vigorous stirring (500 rpm), for about 1 hour. After cooling to room temperature (25° C.), the suspension obtained was filtered, the solid obtained was washed with 5 liters of demineralized water, dried at 120° C. for a night, and subsequently calcined at 500° C. for 5 hours obtaining a silica-alumina ($SiO_2$—$Al_2O_3$) in the form of a colourless powder (48 g), whose elemental analysis, carried out as described above, showed a content of alumina ($Al_2O_3$) equal to 3.8%. Said silica-alumina ($SiO_2$—$Al_2O_3$) had a BET specific surface area, determined as described above, equal to 490 m²/g.

A part of said silica-alumina ($SiO_2$—$Al_2O_3$), 40.4 g, was mixed with 24.4 g of pseudo-bohemite Versal™ V-250 (UOP), as alumina precursor ($Al_2O_3$) of the binder, and 302 ml of a solution at 4% of acetic acid (Aldrich) in a 800 ml beaker. The mixture obtained was kept under vigorous stirring (500 rpm), at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina ($SiO_2$—$Al_2O_3$) with an alumina ($Al_2O_3$) binder, in the form of a colourless solid (53 g) which was subsequently granulated mechanically and the fraction of granules having dimensions ranging from 0.5 mm to 1 mm was used as catalytic material. Said silica-alumina ($SiO_2$—$Al_2O_3$) with an alumina binder ($Al_2O_3$) had a BET specific surface area, determined as described above, equal to 355 m²/g.

EXAMPLE 3

Preparation of a Silica-Alumina ($SiO_2$—$Al_2O_3$) Having a Content of Alumina ($Al_2O_3$) Equal to 8.7%, with an Alumina ($Al_2O_3$) Binder 130 g of aluminium sulfate (Aldrich), as alumina precursor ($Al_2O_3$), and 200 g of demineralized water were introduced into a 500 ml flask: the mixture obtained was maintained at room temperature (25° C.), under vigorous stirring (500 rpm), for about 1 hour, obtaining a limpid solution. Subsequently, 250 g of an aqueous solution of sodium silicate having a silica ($SiO_2$) content equal to 26.5% (Aldrich), as silica precursor ($SiO_2$), were slowly added (15 minutes) to said limpid solution, obtaining a colourless gel. The gel obtained was transferred to a 1 liter beaker and treated 4 times with 500 ml of an aqueous solution of ammonium sulfate at 10% (Aldrich), obtaining a solid. Said solid was filtered, dried at 120° C. for a night, and subsequently calcined at 500° C. for 5 hours, obtaining a silica-alumina ($SiO_2$—$Al_2O_3$) in the form of a colourless powder (64 g), whose elemental analysis, carried out as described above, showed a content of alumina ($Al_2O_3$) equal to 8.7%. Said silica-alumina ($SiO_2$—$Al_2O_3$) had a BET specific surface area, determined as described above, equal to 300 m²/g.

A part of said silica-alumina ($SiO_2$—$Al_2O_3$), 60 g, was mixed with 36 g of pseudo-bohemite Versal™ V-250 (UOP), as alumina precursor ($Al_2O_3$) of the binder, and 200 ml of a solution at 4% of acetic acid (Aldrich) in a 500 ml beaker. The mixture obtained was kept under vigorous stirring (500 rpm), at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina ($SiO_2$—$Al_2O_3$) with an alumina binder ($Al_2O_3$), in the form of a colourless solid (84 g) which was subsequently granulated mechanically and the fraction of granules having dimensions ranging from 0.5 mm to 1 mm was used as catalytic material. Said silica-alumina ($SiO_2$—$Al_2O_3$) with an alumina binder ($Al_2O_3$) had a BET specific surface area, determined as described above, equal to 253 m²/g.

EXAMPLE 4

Preparation of a Silica-Alumina ($SiO_2$—$Al_2O_3$) Having a Content of Alumina ($Al_2O_3$) Equal to 12.8%, with an Alumina ($Al_2O_3$) Binder 171.6 g of an aqueous solution of sodium silicate having a silica ($SiO_2$) content equal to 26.5% (Aldrich), as silica precursor ($SiO_2$), and 40.1 of demineralized water were introduced into a first 500 ml flask, obtaining a first solution. 30.3 g of sodium aluminate (Aldrich), as alumina precursor ($Al_2O_3$), and 271 g of demineralized water were introduced into a second 300 ml flask, obtaining a second solution. Said first and said second solution were poured into a 250 ml flask and kept under vigorous stirring (500 rpm), at room temperature (25° C.), for 1 hour, obtaining a suspension which was subsequently heated to 80° C., and kept under vigour stirring (500 rpm), at said temperature, for 1 hour. After cooling to room temperature (25° C.), the pH of the suspension obtained was brought from pH 13 to pH 12 by adding a solution of sulfuric acid at 96% (Aldrich), obtaining a colourless gel. The gel obtained was transferred to a 1 liter beaker and treated 4 times with 500 ml of an aqueous solution of ammonium sulfate at 10% (Aldrich), obtaining a solid. Said solid was filtered, dried at 120° C. for a night, and subsequently calcined at 500° C. for 5 hours, obtaining a silica-alumina ($SiO_2$—$Al_2O_3$) in the form of a colourless powder (42 g), whose elemental analysis, carried out as described above, showed a content of alumina ($Al_2O_3$) equal to 12.8%. Said silica-alumina ($SiO_2$—$Al_2O_3$) had a BET specific surface area, determined as described above, equal to 163 m²/g A part of said silica-alumina (SiO$_2$—Al$_2$O$_3$), 40.4 g, was mixed with 24.4 g of pseudo-bohemite Versal™ V-250 (UOP), as alumina precursor (Al$_2$O$_3$) of the binder, and 300 ml of a solution at 4% of acetic acid (Aldrich) in a 500 ml beaker. The mixture obtained was kept under vigorous stirring (500 rpm), at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina (SiO$_2$—Al$_2$O$_3$) with an alumina binder (Al$_2$O$_3$), in the form of a colourless solid (56 g) which was subsequently granulated mechanically and the fraction of granules having dimensions ranging from 0.5 mm to 1 mm was used as catalytic material. Said silica-alumina (SiO$_2$—Al$_2$O$_3$) with an alumina binder (Al$_2$O$_3$) had a BET specific surface area, determined as described above, equal to 154 m$^2$/g.

EXAMPLE 5

Preparation of a Silica-Alumina (SiO$_2$—Al$_2$O$_3$) Having a Content of Alumina (Al$_2$O$_3$) Equal to 1.8%, with a Silica (SiO$_2$) Binder 3.8 g of aluminium tri-sec-butoxide (Aldrich), as alumina precursor (Al$_2$O$_3$), were introduced into a first 500 ml flask. 50 g of orthosilicic acid (Aldrich, <20 mesh), as silica precursor (SiO$_2$), and 250 g of demineralized water were introduced into a second 500 ml flask: the suspension of orthosilicic acid obtained was slowly added (10 minutes) to said first flask and the whole mixture was maintained at room temperature (25° C.), under vigorous stirring (500 rpm), for about 2 hours. The suspension obtained was then heated to 90° C., and kept at this temperature, under vigorous stirring (500 rpm), for about 1 hour. After cooling to room temperature (25° C.), the suspension obtained was filtered, the solid obtained was washed with 5 liters of demineralized water, dried at 120° C. for a night, and subsequently calcined at 500° C. for 5 hours obtaining a silica-alumina (SiO$_2$—Al$_2$O$_3$) in the form of a colourless powder (53.4 g), whose elemental analysis, carried out as described above, showed a content of alumina (Al$_2$O$_3$) equal to 1.8%. Said silica-alumina (SiO$_2$—Al$_2$O$_3$) had a BET specific surface area, determined as described above, equal to 501 m$^2$/g.

A part of said silica-alumina (SiO$_2$—Al$_2$O$_3$), 41.1 g, was mixed with 57.7 g of colloidal silica (SiO$_2$) (Ludox® TMA—Sigma-Aldrich), as silica precursor (SiO$_2$) of the binder, and 150 ml of demineralized water in a 800 ml beaker: the mixture obtained was kept under stirring, at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina (SiO$_2$—Al$_2$O$_3$) with a silica binder (SiO$_2$), in the form of a colourless solid (56.3 g) which was subsequently granulated mechanically and the fraction of granules having dimensions ranging from 0.5 mm to 1 mm was used as catalytic material. Said silica-alumina (SiO$_2$—Al$_2$O$_3$) with a silica binder (SiO$_2$) had a BET specific surface area, determined as described above, equal to 357 m$^2$/g.

EXAMPLE 6

Preparation of a Silica-Alumina (SiO$_2$—Al$_2$O$_3$) Having a Content of Alumina (Al$_2$O$_3$) Equal to 3.8%, with a Silica (SiO$_2$) Binder 7.6 g of aluminium tri-sec-butoxide (Aldrich), as alumina precursor (Al$_2$O$_3$), were introduced into a first 500 ml flask. 50 g of orthosilicic acid (Aldrich, <20 mesh), as silica precursor (SiO$_2$), and 250 g of demineralized water were introduced into a second 500 ml flask: the suspension of orthosilicic acid obtained was slowly added (10 minutes) to said first flask and the whole mixture was maintained at room temperature (25° C.), under vigorous stirring (500 rpm), for about 2 hours. The suspension obtained was then heated to 90° C., and kept at this temperature, under vigorous stirring (500 rpm), for about 1 hour. After cooling to room temperature (25° C.), the suspension obtained was filtered, the solid obtained was washed with 5 liters of demineralized water, dried at 120° C. for a night, and subsequently calcined at 500° C. for 5 hours, obtaining a silica-alumina (SiO$_2$—Al$_2$O$_3$) in the form of a colourless powder (48 g), whose elemental analysis, carried out as described above, showed a content of alumina (Al$_2$O$_3$) equal to 3.8%. Said silica-alumina (SiO$_2$—Al$_2$O$_3$) had a BET specific surface area, determined as described above, equal to 490 m$^2$/g.

A part of said silica-alumina (SiO$_2$—Al$_2$O$_3$), 40.3 g, was mixed with 57.2 g of colloidal silica (SiO$_2$) (Ludox® TMA"—Sigma-Aldrich), as silica precursor (SiO$_2$) of the binder, and 150 ml of demineralized water in a 800 ml beaker: the mixture obtained was kept under stirring, at 60° C., for about 2 hours. The beaker was then transferred to a heating plate and the mixture was kept, under vigorous stirring (500 rpm), for a night, at 150° C., until it was dry. The solid obtained was calcined at 550° C., for 5 hours, obtaining a silica-alumina (SiO$_2$—Al$_2$O$_3$) with a silica binder (SiO$_2$), in the form of a colourless solid (55.9 g) which was subsequently granulated mechanically and the fraction of granules having dimensions ranging from 0.5 mm to 1 mm was used as catalytic material. Said silica-alumina (SiO$_2$—Al$_2$O$_3$) with a silica binder (SiO$_2$) had a BET specific surface area, determined as described above, equal to 302 m$^2$/g.

EXAMPLE 7 (COMPARATIVE)

Preparation of a Catalyst Based on Alumina (Al$_2$O$_3$) with an Alumina (Al$_2$O$_3$) Binder 50 g of pseudo-bohemite Versal™ V-250 (UOP), as alumina precursor (Al$_2$O$_3$), were calcined at 500° C., for 5 hours. After cooling to room temperature (25° C.), the solid obtained was mixed with 200 ml of an aqueous solution of acetic acid at 4% (Aldrich) and a further 16.5 g of pseudo-bohemite Versal™ V-250 (UOP), as alumina precursor (Al$_2$O$_3$) of the binder, in a 500 ml beaker. The beaker was then transferred to a heating plate and the mixture was kept, under vigorous stirring (500 rpm), for a night, at 150° C., until it was dry. The solid obtained was calcined at 550° C., for 5 hours, obtaining a catalyst based on alumina (Al$_2$O$_3$) with an alumina binder (Al$_2$O$_3$), in the form of a colourless solid (32.3 g) which was subsequently granulated mechanically and the fraction of granules having dimensions ranging from 0.5 mm to 1 mm was used as catalytic material. Said catalyst based on alumina (Al$_2$O$_3$) with an alumina binder (Al$_2$O$_3$) had a BET specific surface area, determined as described above, equal to 229 m$^2$/g.

Table 1 indicates the various types of catalysts obtained in Examples 1-7.

TABLE 1

| Example | Type | Precursor | Alumina ($Al_2O_3$) (%) | Binder |
|---|---|---|---|---|
| 1 | silica ($SiO_2$) | orthosilicic acid | 0 | alumina ($Al_2O_3$) |
| 2 | silica-alumina ($SiO_2$—$Al_2O_3$) | aluminium tri-sec-butoxide and orthosilicic acid | 3.8 | alumina ($Al_2O_3$) |
| 3 | silica-alumina ($SiO_2$—$Al_2O_3$) | aluminium sulfate and sodium silicate | 8.7 | alumina ($Al_2O_3$) |
| 4 | silica-alumina ($SiO_2$—$Al_2O_3$) | sodium aluminate and sodium silicate | 12.8 | alumina ($Al_2O_3$) |
| 5 | silica-alumina ($SiO_2$—$Al_2O_3$) | aluminium tri-sec-butoxide and orthosilicic acid | 1.8 | silica ($SiO_2$) |
| 6 | silica-alumina ($SiO_2$—$Al_2O_3$) | aluminium tri-sec-butoxide and orthosilicic acid | 3.8 | silica ($SiO_2$) |
| 7 (comparative) | alumina ($Al_2O_3$) | Versal™ V-250 | 100 | alumina ($Al_2O_3$) |

EXAMPLES 8-15

Catalytic Tests

The catalytic materials obtained in Examples 1-7, were used in catalytic dehydration tests of a mixture of alkenols obtained by the catalytic dehydration of 1,3-butanediol operating as described hereunder.

In this respect, the catalyst based on cerium oxide was first prepared, which was used in the dehydration of 1,3-butanediol in order to obtain a mixture of alkenols, operating as described hereunder.

500 g of a commercial aqueous solution at about 30% of ammonium hydroxide ($NH_4OH$), (28%-30% $NH_3$ Basis ACS reagent Aldrich) were added with 500 g of water in a first 3-liter beaker, equipped with a Teflon moon-shaped stirrer shaft, and an electrode was introduced for the measurement of the pH [Metrohm glass electrode for pH (6.0248.030), connected to the pH-meter Metrohom 780]. A solution of 100 g of cerium nitrate hexahydrate (99% Aldrich) was prepared in 1000 g of water in a second 2-liter beaker, equipped with a magnetic anchor stirrer: the cerium nitrate hexahydrate was then solubilized by vigorous stirring (500 rpm), at room (25° C.) temperature. The solution obtained was introduced into a dripper and fed dropwise, over a period of 2 hours, to the solution of ammonium hydroxide ($NH_4OH$) contained in the 3-liter beaker indicated above, under constant vigorous stirring (500 rpm). The pH of the suspension obtained was equal to 10.2. The suspension obtained was filtered and the solid obtained was washed with 2 liters of water and then dried in an oven, at 120° C., for 2 hours. The above synthesis was repeated until 2000 g of solid had been obtained.

1270 g of the solid thus obtained were charged, after sieving at 0.125 mm, into an Erweka planetary mixer with a motor model AMD. The powder was dry mixed for 1 hour and 180 g of an aqueous solution at 25% of ammonium hydroxide ($NH_4OH$), previously prepared by diluting the commercial aqueous solution at 28%-30% (28%-30% $NH_3$ Basis ACS reagent Aldrich), were subsequently added dropwise, in sequence, over a period of 50 minutes, followed by 160 ml of demineralized water, also over a period of 50 minutes, obtaining a paste which was extruded with a Hutt extruder on which rolls with 2 mm holes were assembled. The pellets obtained from the extrusion were left to dry in the air for two days, a batch equal to 100 g was then calcined at 800° C., with a temperature rise of 1° C. per minute up to 800° C., followed by an isotherm at that temperature for 6 hours, obtaining a solid (87.7 g), which was subsequently granulated mechanically and the fraction of granules having dimensions ranging from 0.5 mm to 1 mm was used as catalyst. The catalyst thus obtained, based on cerium oxide, had a BET specific surface area, determined as described above, equal to 5 $m^2/g$.

The fraction of granules having dimensions ranging from 0.5 mm to 1 mm of the catalyst based on cerium oxide obtained as described above, was charged into a reactor, in order to carry out the dehydration reaction of 1,3-butanediol and obtain a mixture of alkenols.

Said dehydration reaction of 1,3-butanediol was carried out in an AISI 316L steel fixed-bed tubular reactor, 400 mm long and with an internal diameter equal to 9.65 mm. A well was present inside the reactor, along its axis, having an external diameter equal to 3 mm which housed the thermocouple for the temperature regulation. The reactor was placed in an oven with electric heating which allowed the temperature selected for the above reaction, to be reached.

The catalyst charge, equal to 3 g, was inserted in the above reactor between two layers of inert material (corundum), the catalytic bed was held in place by means of a sintered steel septum positioned on the bottom of the reactor which had a down-flow configuration.

The feeding was carried out from the top of the reactor, above the area filled with inert material which acted as evaporator and allowed the reagents to reach the reaction temperature before entering into contact with the catalyst.

The liquid reagents were fed by means of a dosing pump of the type used in High Performance Liquid Chromatography (HPLC). The gases were fed by means of a Thermal Mass Flow-meter (TMF). The products obtained were cooled in a heat exchanger, downstream of the reactor, and the condensed liquid was collected in glass bottles using a series of motorized valves. The uncondensed gases, on the other hand, were sent to a wet-gas flow meter, in order to measure the volume of the gases produced. A small part of the gases were sampled in a gas-chromatograph (GC) on-line for analysis. The on-line analysis of the gases was carried out using an Agilent HP7890 gas-chromatograph with a HP-Al/S column having a length of 50 m, a diameter of 0.53 mm, 15 micron film, the carrier used was helium with a flow-rate equal to 30 cm/s, the detector was a flame detector. The analysis of the gases was carried out using an external standard with calibration curves for the single known components.

The characterization of the liquids collected was carried out by means of gas-chromatographic analysis using an Agilent HP6890 gas-chromatograph (GC) equipped with a Split/Splitless injector on a Quadrex 007 FFAP column having a height of 25 mm, a diameter of 0.32 mm, 1 micron film, the carrier used was helium with a rate equal to 50 cm/s, the detector was a flame detector. The determination was carried out using an internal standard with calibration curves for the single known components.

The catalytic performances indicated in Table 2 are expressed calculating the conversion of 1,3-butanediol [1,3-BDO] ($C_{1,3\text{-}BDO}$) and the selectivity ($S_i$) to the various alkenols according to the formulae indicated hereunder:

$$C_{1,3-BDO} = \frac{(moli_{1,3-BDO})_{in} - (moli_{1,3-BDO})_{out}}{(moli_{1,3-BDO})_{in}} \times 100$$

$$S_i = \frac{moli_i}{(moli_{1,3-BDO})_{in} - (moli_{1,3-BDO})_{out}} \times 100$$

wherein:
moles$_i$=moles of alkenols produced (moles of each single i-th alkenol);
(moles$_{1,3-BDO}$)$_{in}$=moles of 1,3-butanediol at the inlet;
(moles$_{1,3-BDO}$)$_{out}$=moles of 1,3-butanediol at the outlet.

The above catalyst based on cerium oxide, ground and sieved in the fraction ranging from 0.5 mm to 1 mm, charged into the reactor as described above, was pre-treated in situ, at 300° C., in a flow of nitrogen (N$_2$).

30 g/h of 1,3-butanediol (Fluka, purity ≥99%), were then fed to the above reactor, together with water in a molar ratio 1,3-butanediol:water equal to 1.2, at atmospheric pressure (1 bara—absolute bar), at the reaction temperatures and times indicated in Table 2.

Table 2 indicates the catalytic results obtained in terms of conversion of 1,3-butanediol [1,3-BDO] ($C_{1,3-BDO}$) and selectivity (S), said selectivity (S) corresponding to the sum of the selectivity (S$_i$) indicated above, i.e. S=ΣS$_i$, calculated as described above, the temperature (° C.) and the reaction time (Time on Stream—T.o.S.) (hours), i.e. the time for which the catalyst was in contact with the feeding stream under the process conditions.

TABLE 2

| Reaction time (T.o.S.) (hours) | Temperature (° C.) | $C_{1,3-BDO}$ (%) | S (%) |
|---|---|---|---|
| 99 | 380 | 83 | 97 |
| 216 | 380 | 84 | 98 |
| 412 | 385 | 85 | 96 |
| 608 | 385 | 88 | 96 |
| 846 | 385 | 86 | 98 |
| 854 | 388 | 88 | 93 |

The mixtures of alkenols leaving the reactor thus obtained were distilled, obtaining an aqueous solution of alkenol isomers having the composition indicated in Table 3.

TABLE 3

| | Composition (%) |
|---|---|
| 2-buten-1-ol | 24 |
| 3-buten-2-ol | 40 |
| 3-buten-1-ol | 0.4 |
| water | 35 |

The mixture of alkenols thus obtained was subjected to catalytic dehydration operating as follows.

The reactor in which said catalytic dehydration reaction was carried out consisted of an AISI 304 stainless steel tubular element having a height (h) equal to 260 mm and an internal diameter (Φ) equal to 10 mm, preceded by and connected to an evaporator, both equipped with electric heating. The outlet of the reactor, on the other hand, was connected to a first condenser connected to a collection flask, and operating at 15° C., in order to allow the recovery of the products obtained from the first dehydration reaction in liquid form at room temperature (25° C.) in said collection flask. Said collection flask was in turn connected to a sampling system consisting of a steel cylinder having a volume (V) equal to 300 ml and equipped at the two ends with interception valves. The vapours/gases deriving from the dehydration reaction and optionally not condensed in the system previously described, could also flow through the above-mentioned steel cylinder, in turn connected to a flow meter which measured its quantity.

The products obtained, both in liquid form and in the form of vapour/gas, were characterized via gas-chromatography, using:
for products in liquid form, a Thermo Trace gas-chromatograph equipped with a FID detector and AQUA-WAX column (Grace 30 m length×0.53 mm internal diameter×1 μm film thickness);
for products in the form of vapour/gas, a 490 micro GC Varian/Agilent gas-chromatograph equipped with 4 channels and with the following columns: Pora Plot Q 10 m long, MolSieve 5 Å 4 m long, Al$_2$O$_3$ 10 m long, with functionality "backflush", CPSil-19 CB 7.5 m long.

The catalytic material used in the form of granules having dimensions ranging from 0.5 mm to 1 mm and in a quantity equal to 3 g, was prepared as described above in Examples 1-7.

The conversion of the alkenols ($C_{ALCH.}$) and the selectivity to 1,3-butadiene ($S_{1,3-BDE}$) were calculated as follows:

$$C_{ALCH.} = \frac{(moles_{ALCH.})_{in} - (moles_{ALCH.})_{out}}{(moles_{ALCH.})_{in}} \times 100;$$

$$S_{1,3-BDE} = \frac{moles_{1,3-BDE}}{(moles_{ALCH.})_{in} - (moles_{ALCH.})_{out}} \times 100;$$

wherein:
(moles$_{ALCH.}$)$_{in}$=moles of alkenols at the inlet;
(moles$_{ALCH.}$)$_{out}$=moles of alkenols at the outlet;
moles$_{1,3-BDE}$=total moles of 1,3-butadiene.

Table 4 indicates: the catalyst used, obtained as described above in Examples 1-7 (Catalyst); the temperature at which the catalytic dehydration is carried out [T (° C.)]; the contact time [τ (s)] calculated as a ratio of the volume of catalytic material charged/volumetric feeding flow-rate; the dilution at which it operates, i.e. the molar ratio water:alkenols in the feed, obtained by adding suitable quantities of water to the mixture of Table 2 [Dilution (mol/mol)]; "Time on Stream", i.e. the time for which the catalyst was in contact with the feeding stream under the process conditions [T.o.S. (hours)]; the selectivity to 1,3-butadiene [$S_{1,3-BDE}$ (%)]; and the conversion of the alkenols [$C_{ALCH.}$(%)].

TABLE 4

| Example | Catalyst | T (° C.) | τ (s) | Dilution (mol/mol) | T.o.S. (hours) | $S_{1,3-BDE}$ (%) | $C_{ALCH.}$ (%) |
|---|---|---|---|---|---|---|---|
| 8 | Example 2 | 300 | 2 | 2.6:1 | 31 | 89 | 100 |
| | | 300 | 2 | 2.6:1 | 54 | 76 | 74 |
| 9 | Example 7 (comparative) | 300 | 2 | 2.6:1 | 29 | 49 | 87 |
| 10 | Example 3 | 300 | 0.5 | 8:1 | 30 | 90 | 73 |
| 11 | Example 4 | 300 | 0.5 | 8:1 | 30 | 81 | 56 |
| 12 | Example 2 | 300 | 0.5 | 8:1 | 29 | 93 | 99 |
| | | 300 | 0.5 | 8:1 | 53 | 74 | 62 |
| 13 | Example 1 | 300 | 2 | 2.6:1 | 27 | 88 | 100 |
| | | 300 | 2 | 2.6:1 | 51 | 78 | 90 |
| 14 | Example 6 | 300 | 2 | 2.6:1 | 24 | 93 | 77 |

TABLE 4-continued

| Example | Catalyst | T (°C.) | τ (s) | Dilution (mol/mol) | T.o.S. (hours) | $S_{1,3\text{-}BDE}$ (%) | $C_{ALCH.}$ (%) |
|---|---|---|---|---|---|---|---|
| 15 | Example 5 | 300 | 2 | 2.6:1 | 30 | 94 | 92 |
| 16 | Example 6 | 350 | 2 | 2.6:1 | 24 | 95 | 100 |
| 17 | Example 2 | 270 | 4 | 2.6:1 | 29 | 88 | 99 |
| 18 | Example 3 | 350 | 0.5 | 8:1 | 6 | 83 | 100 |
| 19 | Example 18 (regenerated) | 350 | 0.5 | 8:1 | 6 | 95 | 100 |

From the data indicated in Table 4, the following results can be observed:
- on comparing Example 8 and Example 9, it can be seen that the catalytic material based on alumina alone ($Al_2O_3$) (content of alumina ($Al_2O_3$) equal to 100%) (Comparative Example 7) has a low selectivity with respect to the catalytic material according to the present invention (Example 8);
- on comparing Examples 10, 11 and 12, it can be seen that with a decrease in the aluminium content in the catalytic material according to the present invention, the productivity of the catalyst increases (higher selectivity and conversion);
- on comparing Example 13 and Example 8, it can be seen that the catalytic material according to the present invention having an alumina content equal to 0% (Example 13) has a selectivity and conversion similar to those of the catalytic material according to the present invention having an alumina content equal to 3.8% (Example 8);
- on comparing Example 14 and Example 15, it can be seen that also in the presence of silica ($SiO_2$) as binder, with a decrease in the alumina content ($Al_2O_3$) in the catalytic material according to the present invention, a higher selectivity and conversion are obtained;
- on comparing Examples 16, 17, 18 and Example 19, it can be seen that the dehydration reaction of the mixture of alkenols can be carried out within a wide range of operating conditions (dilution, temperature, contact times), maintaining good results in terms of selectivity and conversion;
- Example 19 also shows how the catalytic material of Example 18, after regeneration, maintains good results in terms of selectivity and conversion.

In order to obtain the catalytic material used in Example 19, the catalytic material used in Example 18 was subjected to oxidative regeneration. Said oxidative regeneration was carried out by bringing the temperature inside the reactor to 450° C. and subsequently passing a flow of air and nitrogen according to the following procedure:
- Air: 30-60-90-130 ml/min;
- Nitrogen: 100-70-40-0 ml/min;
- Time: 1-1-1-10 hours At the end of the regeneration, the flow of air was interrupted and substituted with nitrogen whereas the reactor was brought to the temperature required for the subsequent test.

The invention claimed is:

1. A process for manufacturing a diene, the process comprising dehydrating at least one alkenol in the presence of at least one catalytic material comprising:
   at least one acid catalyst comprising silica ($SiO_2$) and alumina ($Al_2O_3$), said acid catalyst having a content of alumina lower than or equal to 12% by weight, relative to a total weight of the acid catalyst; and
   optionally a binder.

2. The process according to claim 1, wherein the alkenol is selected from the group consisting of 3-buten-2-ol (methyl vinyl carbinol), 3-buten-1-ol (allyl carbinol), 2-buten-1-ol (crotyl alcohol), and mixtures thereof.

3. The process according to claim 1, wherein the alkenol is directly obtained from a biosynthetic process, or by a catalytic dehydration processes of at least one diol, deriving from a biosynthetic process.

4. The process according to claim 1, wherein the alkenol derives from catalytic dehydration of at least one diol deriving from the fermentation of sugars.

5. The process according to claim 4, wherein the diol is a bio-1,3-butanediol deriving from fermentation of sugars obtained from guayule or thistle, including scraps, residues, waste products deriving from said guayule and/or thistle or from their processing.

6. The process according to claim 1, wherein the acid catalyst is obtained by incipient wetness impregnation wherein a volume of a solution of a metal is equal to or lower than that of a pore volume of a solid support.

7. The process according to claim 1, wherein the acid catalyst is obtained by a process comprising:
   adding, solution or a suspension of silica ($SiO_2$), or its precursors to a solution or a suspension of alumina ($Al_2O_3$), or its precursors, that are selected from the group consisting of aluminium alkoxides and aluminates; adding to said solution or suspension of alumina ($Al_2O_3$), or its precursors, to obtain a solid;
   recovering the solid obtained by precipitation or gelation and;
   optionally subjecting the solid to at least one selected from the group consisting of:
      an ion-exchange in the presence of at least a compound capable of exchanging ions with the surface of the solid selected from aqueous solutions of salts containing ammonium ions,
      a binding step in the presence of at least one precursor of silica ($SiO_2$) selected from colloidal silicas or of at least one precursor of alumina ($Al_2O_3$) selected from boehmite or pseudo-boehmite, and
      a forming step selected from the group consisting of extruding solid, spherulizating the solid, tabletting the solid, and granulating the solid;
   a thermal treatment; and
   a calcination treatment,
   wherein the thermal and calcination treatments, if conducted, are carried out before or after the optional ion-exchange, the optional binding step, or the optional forming step.

8. The process according to claim 1, wherein the acid catalyst has a specific surface area ranging from 50 m$^2$/g to 800 m$^2$/g.

9. The process according to claim 1, wherein the catalytic material comprises the binder, and
   wherein the binder is at least one selected from the group consisting of alumina ($Al_2O_3$), silica ($SiO_2$), zirconium oxide, and titanium oxide.

10. The process according to claim 1, wherein the catalytic material comprises the binder,
    wherein the binder is alumina ($Al_2O_3$) or silica ($SiO_2$), and
    wherein the catalytic material has a specific surface area ranging from 25 m$^2$/g to 700 m$^2$/g.

11. The process according to claim 1, wherein said process is carried out in the presence of a diluent selected from the group consisting of inert gases and compounds having a boiling temperature higher than or equal to 50° C. and a melting temperature lower than or equal to 40° C.

12. The process according to claim 11, wherein said process is carried out:
- if the diluent is selected from inert gases, at a molar ratio between diluent and alkenol higher than 0.3;
- if the diluent is selected from compounds having a boiling temperature higher than or equal to 50° C. and a melting temperature lower than or equal to 40° C., at a molar ratio between diluent and alkenol ranging from 0.01 to 100.

13. The process according to claim 1, wherein said process is carried out:
- at a temperature ranging from 150° C. to 500° C.; and/or
- at a pressure ranging from 0.05 bara (absolute bar) to 50 bara (absolute bar); and/or
- by working at a contact time ($\tau$), calculated as ratio of the volume of catalytic material charged with respect to the volumetric feeding flow-rate, ranging from 0.01 seconds to 10 seconds.

14. The process according to claim 1, wherein the catalytic material is pre-treated at the temperature at which said process is carried out.

* * * * *